United States Patent

Albright

[11] 4,178,330
[45] Dec. 11, 1979

[54] HALOARYL HALOBENZENESULFONATE FLAME RETARDANTS

[75] Inventor: James A. Albright; Ann Arbor, Mich.

[73] Assignee: Velsicol Chemical Corporation, Chicago, Ill.

[21] Appl. No.: 828,581

[22] Filed: Aug. 29, 1977

[51] Int. Cl.$^2$ .............................................. C08K 5/42
[52] U.S. Cl. .................................. 525/3; 260/45.7 S; 260/45.75 B; 260/456 P; 521/121
[58] Field of Search .................... 260/45.7 SF, 456 P, 260/880 R; 424/303; 521/121

[56] References Cited

U.S. PATENT DOCUMENTS

| | | | |
|---|---|---|---|
| 2,028,715 | 1/1936 | Hanson | 252/8.1 |
| 2,678,878 | 5/1954 | Stewart | 260/456 P |
| 3,108,090 | 10/1963 | Leandri et al. | 260/45.7 SF |
| 3,331,797 | 7/1967 | Kopetz et al. | 260/45.75 B |
| 3,387,040 | 6/1968 | Jolles | 260/45.7 S |
| 3,576,770 | 4/1971 | Evans et al. | 260/45.7 RL |
| 3,847,864 | 11/1974 | Chase et al. | 260/45.75 B |
| 3,956,399 | 5/1976 | Paritee et al. | 260/612 R |
| 4,006,118 | 2/1977 | Ogawa et al. | 260/45.95 G |
| 4,116,934 | 9/1978 | Petersen et al. | 260/45.75 B |

OTHER PUBLICATIONS

Slagh et al., J.A.C.S., vol. 72, 1950, p. 2808.

Primary Examiner—Howard E. Schain
Assistant Examiner—R. A. White
Attorney, Agent, or Firm—Dietmar Olesch; R. J. Schwarz

[57] ABSTRACT

Disclosed are haloaryl halobenzene sulfonates of the formula

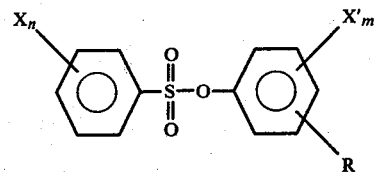

I wherein X and X' are each independently selected halogen, preferably chlorine or bromine; n is a integer of from 1 to 5 and m is an integer from 1 to 4, provided that the sum of n plus m is an integer of from 4 to 9; and R is selected from hydrogen, halogen (preferably chlorine and bromine), and

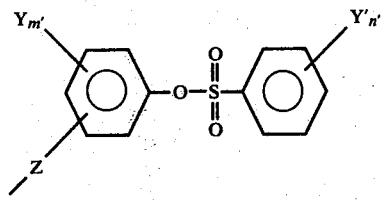

III wherein Y and Y' are each independently selected halogen, preferably chlorine and bromine, m' is an integer from 1 to 4 and n' is an integer of from 1 to 5, provided that m'+n' is from 4 to 9 and Z is an alkylene or alkylidene containing from 1 to 6 carbon atoms. Also disclosed are polymeric compositions containing these compounds as flame retardants.

16 Claims, No Drawings

HALOARYL HALOBENZENESULFONATE FLAME RETARDANTS

BACKGROUND OF THE INVENTION

1. Field of the Invention

This invention relates to haloaryl halobenzene sulfonates and to flame retardant polymeric compositions containing said sulfonates as flame retardants.

2. Description of the Prior Art

During the past several years, a large number of flame retardants have been developed for use with an almost equally large number of flammable materials. Cellulosic materials such as paper and wood and polymeric materials such as polyolefins, polyesters, polyurethane and polystyrene are just two examples of materials for which flame retardants have been developed. For any class of flammable materials, such as synthetic type polymers, those skilled in the art have long been aware that some flame retardant additives are more effective in polymers and polymeric compositions than other flame retardant additives. This is because the efficacy of any flame retardant in polymers or polymeric compositions is measured not only by the flame retardant capability of the additive but also by the ability of the additive to improve or modify, or at least not to detract from, other physical or mechanical properties of the polymer or polymeric compositions. The mere fact, therefore, that some flame retardants contain halogen and sulfur atoms does not assure that any given halogenated or sulfur containing compound will impart usable flame retarding characteristics to all or even to any polymeric system. Furthermore, as those skilled in the art have improved the flame retardancy of many polymeric materials, they have been simultanously required to provide the necessary flame retardancy with a minimal effect upon other properties of the polymer such as the light stability, processability, and flexural, tensile and impact strengths. Also, it has been the desire of those involved in the art of flame retardants to provide flame retardants having a durable lasting effect. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

The prior art considered in the preparation of the instant application in U.S. Pat. Nos. 2,148,928 to Meuron, 2,486,417 to Jackson et al, 2,567,008 to Britton et al., 2,860,168 to Erickson, 3,125,604 to Robbins, 3,228,876 to Larson et al, 3,395,232 to White, 3,818,102 to Partos, 3,850,972 to Garalski, and German patent application No. 2,508,993.

In particular, U.S. Pat. No. 2,148,928 to Meuron discloses mothproofing compositions containing as active ingredients thereof, inter alia, p-chlorobenzene sulphonic acid ester of p-chlorophenol, p-chlorobenzene sulphonic acid ester of phenol, o- m- and p-cresol and their mixture; p-chlorobenzene sulphonic acid ester of o-chlorophenol; p-chlorobenzene sulphonic acid ester of dichlorophenol; p-chlorobenzene sulphoic acid ester of p-amylphenol; di-(p-chlorobenzene sulphonic acid ester) of dihydroxy-diphenyl, di-(p-chlorobenzene sulphonic acid ester) of dihydroxy-diphenyl sulphone; di-(p-chlorobenzene sulphonic acid ester) of diphenolisatin; 3,4-dichlorobenzene sulphonic acid ester of o- or p-chlorophenol; and 2,5-dichlorobenzene sulphonic acid ester of o- or p-chlorophenol. This patent fails to disclose the instant compounds of formula I wherein $m+n=4$ to 10, and their use as flame retardants in polymeric compositions.

U.S. Pat. No. 2,567,008 to Britton et al discloses aryl esters of 4-chlorobenzene sulfonic acid of the formula

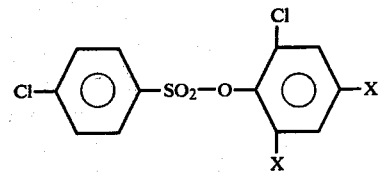

wherein one X represents a phenyl radical and the other X represents hydrogen. These compounds are disclosed as being of value as toxic constituents of parasiticidel compositions. This patent fails to teach the instant compounds or their efficacy as flame retardants for polymeric compositions.

U.S. Pat. No. 3,850,972 to Goralski discloses phenyl esters of bromo-methanesulfonic acid corresponding to the formula

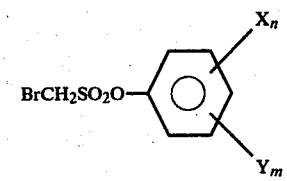

wherein X represents halo, halo lower alkoxy, nitro, trifluoromethyl, or phenoxy and n represents an integer from 1 to 5 for halo groups and from 0 to 1 for groups other than halo; Y represents halo, nitro, or lower alkyl; m represents an integer from 0 to 2; and $m+n$ does not exceed 5. These compounds are disclosed as having antimicrobal and fire retardant activity.

German Pat. No. 2,508,993 discloses flame retardant aryl mono- or di-sulphonic acid esters of polybromo phenols of the formula

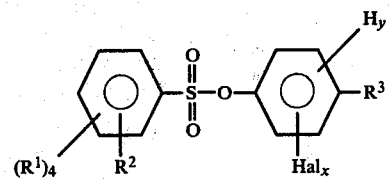

where $R^1$ is H, 1-8 carbon alkyl, Br or Cl; $R^2$ is the same as $R^1$ or is

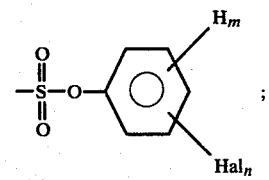

Hal is Br or Cl; x is 2-4, n is 3-5; y is $4-x$, $m=5-n$, $R^3$ is Br, cl or

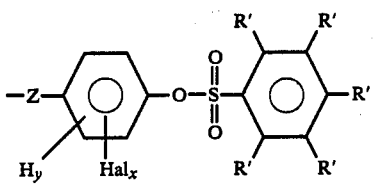

where Z is —O—, —S—, —s(O)₂—, 1-4 carbon alkylene or alkylide.

These compounds are disclosed as being flame-retardants in polyolefins, especially polyethylene and polypropylene.

SUMMARY OF THE INVENTION

In accordance with this invention there are provided haloaryl halobenzenesulfonates of the generic formula

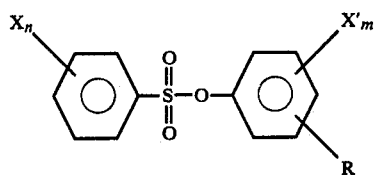

I where X and X' are each independently selected halogens, preferably chlorine and bromine; n is an integer of from 1 to 5 and ma is an integer of from 1 to 4, provided that m+n is an integer of from 4 to 9; and R is independently selected from hydrogen, halogen (preferably chlorine and bromine); and

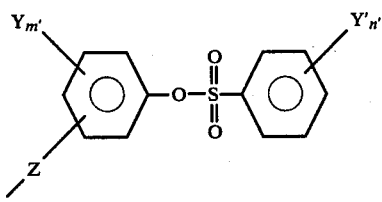

III wherein Y and Y' are each independently selected halogen (preferably chlorine and bromine), m' is an integer of from 1 to 4 and n' is an integer of from 1 to 5, provided that m'+n' has a value of from 4 to 9, and Z is an alkylene or aklylidene of from 1 to 6 carbon atoms. The haloaryl halobenzenesulfonates of the present invention are particularly well adapted for flame retarding polymeric composition, particularly polyolefins, polystyrenes, and polyurethanes.

DESCRIPTION OF THE PREFERRED EMBODIMENTS

The haloaryl halobenzenesulfonates within the scope of this invention are described by formula I and include the following exemplary compounds: 2,4,6-tribromophenyl-2',4',5',-trichlorobenzene sulfonate, pentabromophenyl-2,4,5-trichlorobenzene sulfonate, pentabromophenyl-2',4',5'-tribromobenzene sulfonate, pentabromophenyl-pentabromobenzene sulfonate, pentabromophenyl-2',5'-dibromobenzene sulfonate, 2,4-dichlorophenyl-2',4'-dichlorobenzene sulfonate, 2,3,5,6-tetrachlorophenyl-pentabromobenzene sulfonate, 2,2-bis-[3,5-dibromo-4-(2',4',5'-tetrachlorobenzene sulfonato) phenyl] propane, 1,2-bis-[2,3,5,6-tetrabromo-4-(2',4',5'-tribromobenzene sulfonato) phenyl]ethane,2-[3,5-dibromo-4-(2',3',4',5'-tetrachlorobenzene sulfonato) phenyl]-2-[2,3,5-tribromo-4-(2',4',5'-trichlorobenzene sulfonato) phenyl] propane, and 2-[3,5-dibromo-4-(2',4',5'-trichlorobenzene sulfonato) phenyl]-2-[2,3,5,6-tetrabromo-4-(2',4',5'-triromobenzene sulfonato) phenyl] propane. For purposes of illustration only, Table I as follows is designed to further help describe the compounds of this invention and is neither meant nor should it be taken to be a complete listing of all the compounds within the scope of this invention as described by formula I.

A preferred group of compounds are those of formula I wherein R is selected from the group consisting of halogen, preferably chlorine and bromine, and hydrogen. This sub-generic group of compounds are hereinafter referred to as group II compounds. Of these group II compounds, compounds wherein R is halogen, preferably chlorine and bromine, are more preferred.

Another preferred group of compounds are those of formula I wherein R is

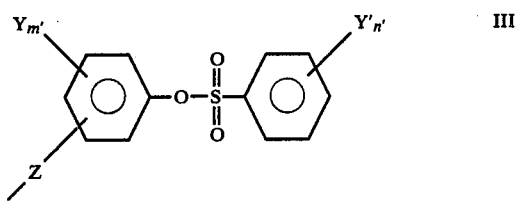

III with Z, Y, Y', m' and n' being defined above. This sub-generic group of compounds are hereinafter referred to as group III compounds.

The haloaryl halobenzenesulfonates within the scope of this invention, more particularly compounds of formula I wherein R is selected from the group consisting of hydrogen and halogen, preferably chlorine and bromine, i.e., group II compounds, may generally be prepared according to the following reaction scheme:

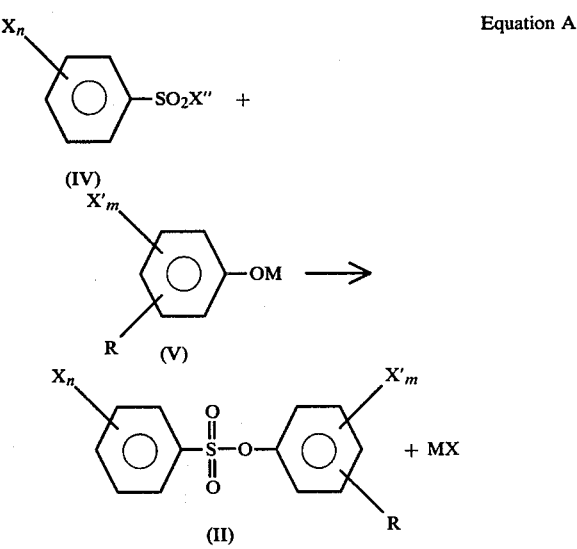

Equation A wherein X, X', n and m are as defined above, R is selected from the group consisting of hydrogen and halogen, preferably chlorine and bromine, X" is halogen, and M is an alkali metal or alkaline earth metal.

More particularly, the reaction of Equation A is generally carried out by the reaction of equimolr quantities of the desired compound of formula IV with the desired compound of formula V.

TABLE I

| Compound | X | X' | N | M | R | Z | Y | Y' | M' | N' |
|---|---|---|---|---|---|---|---|---|---|---|
| 1 | Cl | Br | 1 | 3 | H | — | — | — | — | — |
| 2 | Cl | Br | 3 | 3 | H | — | — | — | — | — |
| 3 | Cl | Br | 5 | 4 | Br | — | — | — | — | — |
| 4 | Br | Br | 2 | 2 | H | — | — | — | — | — |
| 5 | Br | Cl | 1 | 3 | Br | — | — | — | — | — |
| 6 | Cl | Br | 3 | 3 | Br | — | — | — | — | — |
| 7 | Br | Br | 3 | 4 | Br | — | — | — | — | — |
| 8 | Cl | Cl | 3 | 4 | Cl | — | — | — | — | — |
| 9 | Cl | Cl | 2 | 2 | Br | — | — | — | — | — |
| 10 | Cl | Br | 3 | 2 | H | — | — | — | — | — |
| 11 | Cl | Br | 3 | 2 | 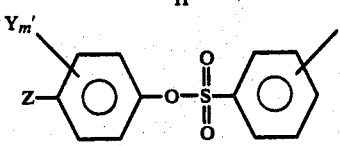 | $-\overset{CH_3}{\underset{CH_3}{C}}-$ | Br | Cl | 2 | 3 |
| 12 | Br | Br | 3 | 4 |  | $-CH_2CH_2-$ | Br | Cl | 2 | 3 |
| 13 | Cl | Br | 3 | 2 | 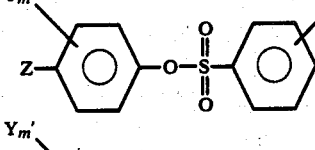 | $CH_2$ | Br | Br | 2 | 5 |
| 14 | Br | Br | 3 | 3 | 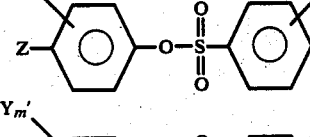 | $-\overset{CH_3}{\underset{CH_3}{C}}-$ | Br | Br | 3 | 3 |
| 15 | Cl | Cl | 3 | 3 | 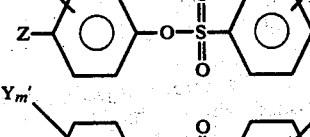 | $Y'_m-CH_2CH_2CH_2-$ | Cl | Cl | 2 | 3 |

The reaction conditions are such that compounds IV coreact with compounds V to produce compounds II. Generally, the reaction can be carried out at a temperature between about 25° to about 150° C. in the presence of an inert organic solvent such as dimethylformamide, dimethyl sulfoxide, and the like. Usually atmospheric or supraatmospheric pressures are employed during the reaction. The reaction is generally carried out from about 1 to about 10 hours but the time is usually dependent on the chosen temperatures and pressures at which the reaction is carried out.

The haloaryl halobenzenesulfonates within the scope of this invention, more particularly compounds of formula I wherein R is

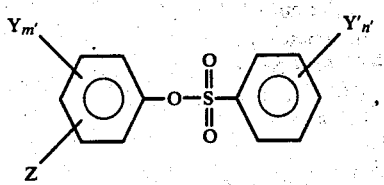

i.e., group III compounds, may generally be prepared according to the following reaction scheme:

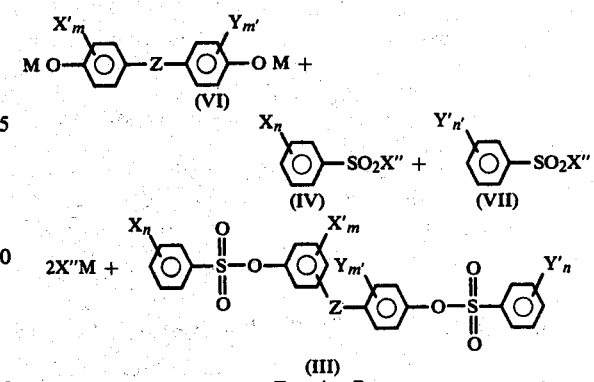

(III)
Equation B wherein X,X',X",Y,Y',n,n',m,m', and M are defined above.

More particularly, the reaction of Equation B is generally carried out by the reaction of equimolar quantities of the desired compound of formula VI with the desired compounds of formulas IV and VII. The reaction conditions are such that compounds VI coreact with compounds IV and VII to produce compounds III. Generally, the reaction can be carried out at a temperature between about 25° to about 150° C. in the presence of an inert organic solvent such as dimethylformamide, dimethyl sulfoxide, and the like. Usually atmospheric or supraatmospheric pressures are employed during the reaction. The reaction is generally carried out from about 1 to about 10 hours but the time is usually dependent on the chosen temperatures and pressures at which the reaction is carred out.

The compounds of formula I are useful flame retardants in polymeric compositions selected from the group consisting of polyurethane, including flexible and rigid foams and elastomers, polyolefins, e.g., polypropylene, and styrene polymers such as polystyrene, including both crystalline and high impact types, and styrene co and terpoloymers such as styrene-butadiene copolymer, styrene-acrylonitrile copolymer and acrylonitrilebutadiene-styrene terpolymers. A further description of the above polymers applicable to the present invention may be found in Modern Plastic Encyclopedia, Vol. 53, No. 10A, pp. 607, 81–84, and 86–96, McGraw-Hill, Inc., New York, New York (1976), said publication being incorporated herein by reference.

It is also contemplated that the flame retardants of formula I will possess flame retardant efficacy in polyester, both saturated and unsaturated. A detailed description of polyester polymers can be found on pages 51–61 of Modern Plastic Encyclopedia, ibid, incorporated herein by reference.

The flame retardants of this invention may be incorporated into or applied onto the various flammable polyurethane, polyolefin, and styrene polymeric materials by techniques which are standard or known to those skilled in the art. See, for example, J. M. Lyons "The Chemistry and Uses of Fire Retardants", Wiley-Interscience, New York, N.Y. (1970) and Z. E. Jolles, "Bromine and Its Compounds", Academic Press, New York, N.Y. (1966). The amount of the flame retardant compound of the present invention incorporated into the polymeric system is an amount effective to render said polymeric system flame retardant. Generally, this is, in percent by weight, from about 1% to about 50%. Usually, depending on the substate and the amount of flame retardancy desired, up to about 40 weight percent of the flame retardant compound within the scope of this invention can be incorporated therewith. However, in most applications it is preferred to use less than 25 weight percent of said compounds within the scope of this invention. It should be noted that the optimum level of additive of the flame retardant within the scope of this invention depends upon the particular substrate being treated as well as the level of flame retardancy desired. For example, in polyurethanes a flame retardant level of from about 10 to 35 percent by weight of the total polymeric compositions is satisfactory.

In addition to the flame retardant compounds within the scope of this invention, the flame retardancy of a polymer can be further enhanced through the use of so called "synergists" or enhancing agents which when used with the compounds of formula I promote a cooperative effect therebetween and thus enhance the flame retardancy of the resultant plastic composition as compared to the flame retardancy of either one component aused separately. These "enhancing agents" comprise the oxides and halides of groups IVA and VA of the Periodic Table, i.e., oxides and halides of antimony, bismuth, arsenic, tin, lead, germanium, e.g., antimony oxychloride, antimony chloride, antimony oxide, stannic oxide, stannic chloride, arsenous oxide, arsenous chloride, and the like; and organic and inorganic compounds of phosphorus, nitrogen, boron, and sulfur, e.g., triphenyl phosphate, ammonium phosphate, zinc borate, thiourea, urea, stannic sulfide, and the like and oxide and halides of titanium, vanadium, chromium, manganese, iron, niobium, molybdenum copper, zinc, magnesium, e.g., titanium dioxide, titanium chloride, vanadium pentoxide, chromic bromide, manganous oxide, molybdenum trioxide, ammonium molybdate; and hydrates of the above, e.g., stannic oxide hydrate, lead hydrate; and combinations thereof. The preferred enhancing agents are the oxides of antimony, arsenic and bismuth. However, any compound which on decomposition, as by ignition, yields these oxides would be suitable. Thus, some organic antimonates are preferred. The enhancing agents disclosed in U.S. Pat. Nos. 3,205,196, 2,996,528 and 2,993,924 are also suitable for use and these patents are to be considered as incorporated herein by reference. Without limitation, preferred enhancing agents include $Sb_2O_3$, $SbCl_3$, $SbBr_3$, $SbI_3$, $SbOCl$, $As_2O_5$, $ZnBO_4$, $BaB_2O_4 \cdot H_2O$, $2 \cdot ZnO \cdot 3 \cdot B_2O_3 \cdot 3.5H_2O$ and stannic oxide hydrate. The more preferred enhancing agent is antimony trioxide.

It is also within the scope of the present invention to employ other materials in the present invention compositions where one so desired to achieve a particular end result. Such materials include, without limitations, adhesion promotors; antioxidants; antistatic agents; antimicrobials; colorants; flame retardants such as those listed on pages 654–660, Modern Plastic Encyclopedia, ibid., (in addition to the new class of flame retardants described herein); heat stabilizers; light stabilizers; pigments; plasticizers; preservatives; ultraviolet stabilizers and fillers.

In this latter category, i.e., fillers, there can be mentioned without limitation, materials such as glass, carbon, cellulosic fillers (wood flour, cork, and shell flour); calcium carbonate (chalk, limestone, and precipitated calcium carbonate); metal flakes; metallic oxides (aluminum, beryllium oxide and magnesia); metallic powders (aluminum, bronze, lead, stainless steel and zinc); polymers (comminuted polymers and elastomerplastic blends); silica products (diatomaceous earth, novaculite, quartz, sand, tripoli, fumed colloidal silica, silica aerogel, wet process silica); silicates (asbestos, kaolinite, mica, nepheline, syenite, talc, wollastonite, aluminum silicate and calcium silicate); and inorganic compounds such as barium ferrite, barium sulfate, molybdenum disulfide and silicon carbide.

The above mentioned materials, including filler, are more fully described in Modern Plastic Encyclopedia, ibid., which publication has been incorporated herein by reference.

The amount of the above described materials employed in the present invention compositions can be any quantity which will not substantially adversely affect the desired results from the present invention compositions. Thus, the amount used can be any amount up to that percent based on the total weight of the composition at which said composition can still be classified as a plastic. In general, such amount will be from about 0% to about 75% and more specifically from about 1% to about 50%.

The following examples are provided for the purpose of further illustration only and are not intended to be limitations on the disclosed invention. Unless otherwise specified, all temperatures are expressed in degrees Centigrade and all volumes are in milliliters.

EXAMPLE 1

Preparation of 2,4,6-tribromophenyl-2',4',5'-trichlorobenzene sulfonate. Tribromophenol (66.2 grams) is dissolved with 200 ml of dimethylformamaide in a three neck, one liter flask. Sodium hydroxide (3 grams) is added to the fsolution and the solution is heated at 52° C. for about one hour. Then 56 grams of 2,4,5-trichlorobenzenesulfonyl chloride is added and the solution is heated at 80° to 90° C. for about 2 hours. The reaction mixtures is cooled to about 25° to 30° C. and 350 ml of 10% sodium hydroxide is added. A white precipitate forms which is filtered. The white solid is washed twice with ethanol to yield 61 grams of product.

EXAMPLE 2

Preparation of pentabromophenyl-2,4,5-trichlorobenzene sulfonate. Ninety-eight grams of pentabromophenol are dissolved in 200 ml of dimethyl-formamide. Sodium hydroxide (8 grams) is then added and the resulting mixture is heated until all the sodium hydroxide is dissolved. Trichlorobenzene sulfonyl chloride (56 grams) is then added and the resulting solution is heated to 80° C. for 5 hours. The solution is then cooled and diluted with water. The solution is made basic with sodium hydroxide and filtered. The precipitate is washed several times with water to obtain 129 grams of product, having a melting point of 180°–182° C.

EXAMPLE 3

Preparation of pentabromophenyl-2,5-dibromobenzene sulfonate. Sodium pentabromophenate (488 grams) is added to 334 grams of p-dibromobenzenesulfonyl chloride in 500 ml. of dimethylformamide at 95° C. in a portionwise manner. After addition to complete the reaction mixture is heated to 120° C. for one hour. The reaction mixture is then cooled to 60° C. and poured into 2 liters of cold water. A precipitate is formed, filtered, washed twice with water and dried for 6 hours to obtain 412 grams of product, having a melting point of 175°–182° C.

EXAMPLE 4

Preparation of 2,2-bis-[3,5-dibromo-4-(2',4',5'-trichlorobenzene sulfonato)phenyl] propane.

To a solution of 272 grams of tetrabromobisphenol A in 250 ml. of dimethylformamide is added 40 grams of sodium hydroxide. The mixture is heated to 100° C. and stirred for two hours. The reaction mixture is cooled to 30° C. and 280 grams of trichlorobenzenesulfonyl chloride are then added portionwise. After addition of the trichlorobenzene sulfonyl chloride is complete the reaction mixture is heated at 85° C. for two hours. The reaction mixture is then poured into water, filtered and dried. 410 grams of product, having a melting point of 198°–204° C. are obtained.

EXAMPLE 5

A solution of 600 grams of polystyrene and 10 parts per hundred resin (phr) of the compound of Example 2 in 2,670 grams of methylene chloride and 60 grams of hexane is prepared. To the above solution is added 3 grams of dicumyl peroxide as a flame retardant synergist. This mixture is poured into an aluminum dish and the methylene chloride is allowed to evaporate in the air. Following this, the casting is steamed to produce a crude foam. This foam is then cut into sufficient specimens of appropriate sizes in order to subject said foam to an Oxygen Index Test (O.I.), ASTM D-2863-70.

Additional samples of polymer are prepared in which the amount of fire retardant is 5 phr and 0 phr (control). The results obtained by subjecting the foamed specimens to the Oxygen Index Test are listed in Table II.

Table II

| Flame Retardant | phr | O.I. |
| --- | --- | --- |
| (control) | 0 | 19.5 |
| Compound of Example 2 | 5 | 23.0 |
| Compound of Example 2 | 10 | 24.5 |

EXAMPLE 6

A rigid polyurethane foam is prepared using the following basic formulation:

| Component | Parts by weight |
| --- | --- |
| Polyol[a] | 100 |
| Silicone Glycol[b] Surfactant | 2 |
| Trichlorofluoromethane[c] | 35 |
| Polyisocyanate[d] | 135 |

[a] alkanolamine polyol, molecular weight approximately 3500, hydroxyl number approximately 530, Thanol R-350-X Jefferson Chemical Co., Houston, Texas.
[b] Dow Corning 193, Dow Corning Corp., Midland, MI.
[c] Freon 11B, E.I. DuPont de Nemours & Co., Wilmington, Del.
[d] Polymeric Aromatic isocyanate, 31.5% available NCO, Mondur MRS, Mobay Chemical Co., Pittsburgh, PA.

the polyol, surfactant, and fluorocarbon blowing agent are combined in a master batch based on 1000 g of polyol to minimize loss of blowing agent.

The following procedure is used to prepare the foam:
1. The polyisocyanate is weighted into a tared, 10 ounce, paper cup (allowances being made for hold-up) and the cup set aside while the remaining ingredients are weighted out and mixed.
2. The polyol masterbatch is weighted out, in the proper amount to give 100 grams of polyol, in one quart, untreated, paper cup.
3. The 30 grams of the compound of Example 3 are then weighted into the same one quart cup.
4. The contents of the one quart cup are mixed at 1000 rpm for 5 seconds.
5. The polyisocyanate is then added and stirring at 1000 rmp continues for 10 seconds.
6. The mix is poured into a 5 pound, untreated, paper tub and allowed to rise.

After the foam is tack-free, and substantially cured, it is set aside for at least seven days prior to subjecting said foam to an Oxygen Index Test, ASTM D-2863-70. Following the above procedure except the flame retardant was omitted, a second foam composition was prepared, as a control. The results of the Oxygen Index Test are reported in Table III below.

Table III

| Flame Retardant | Load Level, php | O.I., % |
| --- | --- | --- |
| control | 0 | 21.0 |
| compound of Example 3 | 30 | 24.0 |

EXAMPLE 7

The designated flame retardant, antimony trioxide and polystyrene (Cosden 925 TV-K brand high impact polystyrene, Cosden Oil Chemical Company, Big Springs, Texas) were compounded using a C.W. Brabender Prep-Center fitted with a high shear compounding mixer. Each charge was compounded at 200° C. and 120 rmp for 2 to 3 minutes. After cooling to room temperature the mass was ground. Each flame retarded polymer system was then let down to the desired level of 15 weight percent flame retardant, 3 percent antimony trioxide and 82 percent polymer by dry blending the ground concentrate and additional amounts of polymer. The resulting polymer system was then injection molded using a Newbury 30 ton injection molding machine. The molded specimens were subjected to various tests and the data derived from these tests are reported in Table IV below.

Table IV

| Test | Flame Retardant of Example | |
|---|---|---|
| | 1 | 2 |
| Flammability, UL-94 dated February 1, 1974 | | |
| 1/8 inch thick | V-0 | V-0 |
| 1/16 inch thick | V-2 | V-0 |
| Notched Izod Impact, ASTM D-256-72a | 1.97 | 2.1 |
| Gardner Impact | 14 | 17 |
| Heat Distortion Temperature, ASTM D-648-72, at 264 psi, °F. | 163 | 157 |
| Melt Flow Index, ASTM 1238-70, Condition G, 200° C. 5000 g, grams/10 minutes | 11.3 | 14.3 |

EXAMPLE 8

The designated flame retardant, antimony trioxide acrylonitrile-butadiene-styrene (ABS) polymer (Cycolac and GSM 4500 brand ABS, Borg Warner Chemical Company, Chicago, Illinois) were compounded using a C.W. Brabender Prep-Center fitted with a high shear compounding mixer. Each charge was compounded at 200° C. and 120 rpm for 2 to 3 minutes. After cooling to room temperature the mass was ground. Each flame retarded polymer system was then let down to the desired level of 22 weight percent flame retardant, 4.4 percent antimony trioxide and 73.6 percent polymer by dry blending the ground concentrate and additional amounts of polymer. The resulting polymer system was then injection molded using a Newbury 30 ton injection molding machine. The molded specimens were subjected to various tests and the data derived from theses tests are reported in Table V below.

Table V

| Test | Flame Retardant of Example 2 |
|---|---|
| Flammability, UL-94 dated February 1, 1974 | |
| 1/8 inch thick | V-0 |
| 1/16 inch thick | V-0 |
| Notched Izod Impact, ASTM D-256-72a | 1.5 |
| Heat Distortion Temperature, ASTM D-648-72, at 264 psi, °F. | 150 |

EXAMPLE 9

The flame retardant, antimony trioxide (when added) and Pro-fax 6823 polypropylene base resin was compounded using a C.W. Brabender Prep-Center fitted with a high shear compounding mixer. (Pro-fax 6823 is a trade mark of Hercules Incorporated, Wilmington, Delaware 19899). The flame retardant additive was dry blended with the polypropylene. Since the capacity of the mixing bowl was only 300 grams, a dip technique for compounding was utilized which consisted of fluxing 300 grams of the dry blend mixture and the removal of approximately 200 grams of the fluxed mixture followed by the addition of more of the dry blend mixture until the total dry blend had be compounded. Each charge was compounded under the same conditions: 200° C. temperature, 400 rmp, with 2 to 3 minute compounding time. The flame retarded polymer systems were injection molded using a Newbury 30 ton injection molding machine. The above prepared resins were subjected to various tests and the data derived from said tests are reported in Table VI below.

Table VI

| | A | B |
|---|---|---|
| Composition (weight percent) | | |
| Flame retardant of Example 1 | 5 | 3 |
| Antimony trioxide | 0 | 1.5 |
| Polypropylene | 95 | 95.5 |
| | 100 | 100 |
| Test | | |
| Flammability UL-94, dated February 1, 1974 | | |
| Vertical- | | |
| 1/8 inch thick | V-2 | V-2 |
| 1/16 inch thick | V-2 | V-2 |
| Horizontal burn | | |
| 1/8 inch thick | P | P |
| 1/16 inch thick | P | P |
| Notched Izod Impact ASTM D-256-72A | 1.6 | 1.7 |
| Melt Index | 2.8 | 2.5 |

The above examples in the foregoing specifications are for the purpose of illustration and not limitation. Many modifications and ramifications will naturally suggest themselves to those skilled in the art base on this disclosure. These are intended to be comprehended as within the scope of this invention.

The embodiments of the invention in which an exclusive property or privilege is claimed are defined as follows:

1. A flame retardant polyurethane composition comprising polyurethane and a flame retardant amount of haloaryl halobenzene sulfonate of the formula

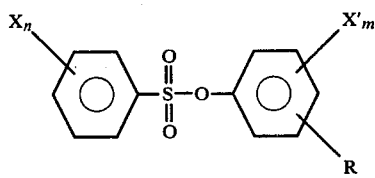

wherein X and X' are each independently selected halogen; n in an integer from 1 to 5 and m is an integer from 1 to 4, provided that the sum of m plus n is an integer from 4 to 9; and R is selected from the group consisting of hydrogen, halogen, and

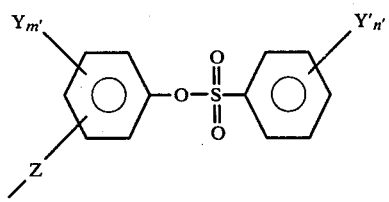

wherein Y and Y' are each independently selected halogen, M' is an integer from 1 to 4 and n' is an integer from 1 to 5, provided that the sum of m' plus n' is an integer from 4 to 9; and wherein Z is an alkylene or alkylidene group containing from 1 to about 6 carbon atoms.

2. The composition of claim 1, wherein said halogen is chlorine or bromine.

3. The composition of claim 2, wherein R is selected from the group consisting of hydrogen, chlorine, and bromine.

4. The composition of claim 2, wherein R is

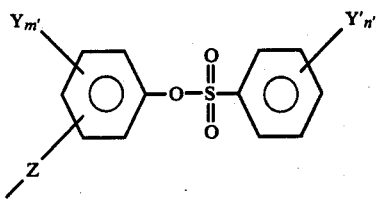

5. The composition of claim 1, wherein said sulfonate is 2,4,6-tribromophenyl-2',4',5'-trichlorobenzene sulfonate.

6. The composition of claim 1, wherein said sulfonate is pentabromophenyl-2,4,5-trichlorobenzene sulfonate.

7. The composition of claim 1, wherein said sulfonate is pentabromophenyl-2,5-dibromobenzene sulfonate.

8. The composition of claim 1, wherein said sulfonate is 2,2-bis-[3,5-dibromo-4-(2',4',5'-trichlorobenzene sulfonateo) phenyl] propane.

9. A flame retardant acrylonitrile-butadiene-styrene polymer composition comprising acrylonitrile-butadiene-styrene polymer and a flame retardant amount of haloaryl halobenzene sulfonate of the formula

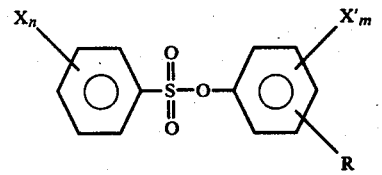

wherein X and X' are each independently selected halogen; n is an integer from 1 to 5 and m is an integer from 1 to 4, provided that the sum of m plus n is an integer from 4 to 9; and R is selected from the group consisting of hydrogen, halogen, and

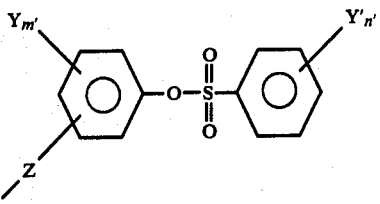

wherein Y and Y' are each independently selected halogen, m' is an integer from 1 to 4 and n' is an integer from 1 to 5, provided that the sum of m' plus n' is an integer from 4 to 9; and wherein Z is an alkylene or alkylidene group containing from 1 to about 6 carbon atoms.

10. The composition of claim 9, wherein said halogen is chlorine or bromine.

11. The composition of claim 10, wherein R is selected from the group consisting of hydrogen, chlorine, and bromine.

12. The composition of claim 10, wherein R is

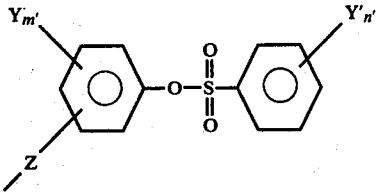

13. The composition of claim 9, wherein said sulfonate is 2,4,6-tribromophenyl-2',4',5'-trichlorobenzene sulfonate.

14. The composition of claim 9, wherein said sulfonate is pentabromophenyl-2,4,5-trichlorobenzene sulfonate.

15. The composition of claim 9, wherein said sulfonate is pentabromophenyl-2,5-dibromobenzene sulfonate.

16. The composition of claim 9, wherein said sulfonate is 2,2-bis-[3,5-dibromo-4-(2',4',5'-trichlorobenzene sulfonateo) phenyl] propane.

* * * * *